United States Patent [19]

Raynes et al.

[11] Patent Number: 5,568,815
[45] Date of Patent: Oct. 29, 1996

[54] SELF-POWERED INTERFACE CIRCUIT FOR USE WITH A TRANSDUCER SENSOR

[75] Inventors: John W. Raynes, Sandy, Utah; Gary Altman, Kirkland, Wash.

[73] Assignee: Becton Dickinson and Company, Franklin Lakes, N.J.

[21] Appl. No.: 342,498

[22] Filed: Nov. 21, 1994

[51] Int. Cl.[6] ........................................ A61B 5/00
[52] U.S. Cl. ..................... 128/672; 128/673; 128/675; 128/748
[58] Field of Search ........................ 128/668, 672, 128/673, 675, 734, 748, 736

[56] References Cited

U.S. PATENT DOCUMENTS

| | | | |
|---|---|---|---|
| 3,880,006 | 4/1975 | Poduje | 73/362 |
| 4,190,886 | 2/1980 | Sherman | 364/415 |
| 4,202,218 | 5/1980 | Romo | 73/766 |
| 4,223,682 | 9/1980 | Sherman | 128/672 |
| 4,337,665 | 7/1982 | Sato et al. | 73/766 |
| 4,362,060 | 12/1982 | Okayama et al. | 73/708 |
| 4,420,000 | 12/1983 | Bailey | 128/706 |
| 4,444,056 | 4/1984 | Romo | 73/708 |
| 4,446,715 | 5/1984 | Bailey | 73/1 R |
| 4,459,993 | 7/1984 | Foreman | 128/706 |
| 4,478,224 | 10/1984 | Bailey | 128/706 |
| 4,480,478 | 11/1984 | Sato et al. | 73/708 |
| 4,556,807 | 12/1985 | Yamada et al. | 307/491 |
| 4,667,516 | 5/1987 | Schulz | 73/708 |
| 4,672,974 | 6/1987 | Lee | 128/673 |
| 4,705,047 | 11/1987 | Bailey | 128/672 |
| 4,715,003 | 12/1987 | Keller et al. | 364/571 |
| 4,765,188 | 8/1988 | Krechmery et al. | 73/708 |
| 4,798,093 | 1/1989 | Kenoun | 73/708 |
| 4,836,027 | 6/1989 | Hannappel et al. | 73/708 |
| 4,883,992 | 11/1989 | Koglin et al. | 307/491 |
| 4,911,016 | 3/1990 | Miyazaki et al. | 73/766 |
| 4,979,940 | 12/1990 | Bobo, Jr. et al. | 604/50 |
| 5,006,835 | 4/1991 | Griswold et al. | 340/626 |
| 5,012,411 | 4/1991 | Policastro et al. | 364/413.06 |
| 5,042,307 | 8/1991 | Kato | 73/708 |
| 5,099,695 | 3/1992 | Sugano et al. | 73/708 |
| 5,117,835 | 6/1992 | Mick | 128/748 |
| 5,135,002 | 8/1992 | Kirchner et al. | 128/672 |
| 5,193,547 | 3/1993 | Evans, II et al. | 128/668 |
| 5,325,865 | 7/1994 | Beckman et al. | 128/748 |

*Primary Examiner*—Angela D. Sykes
*Assistant Examiner*—Stephen Huang
*Attorney, Agent, or Firm*—Eric M. Lee, Esq.

[57] ABSTRACT

An interface circuit for interfacing a semiconductor transducer sensor to a patient vital signs monitor is disclosed. In one embodiment, the interface circuit includes a power supply circuit that receives an excitation power signal generated by the patient monitor, and derives therefrom unregulated and regulated supply voltages for use by the electrical components on the interface circuit. Also generated by the power supply circuit is an appropriate sensor excitation signal for the semiconductor transducer. In another embodiment, the interface circuit further includes receiving circuitry for receiving a sensor output signal generated by the transducer sensor. A scaling circuit then scales that signal into a parameter signal that is proportional to the physiological condition detected by the sensor, and that is also proportional to the excitation power signal generated by the patient monitor. If necessary, the interface circuit further includes isolation circuitry, for electrically isolating the transducer sensor from the patient monitor.

42 Claims, 5 Drawing Sheets

SELF-POWERED INTERFACE CIRCUIT FOR USE WITH A TRANSDUCER SENSOR

BACKGROUND OF THE INVENTION

1. Technical Field

The present invention relates generally to systems for measuring physiological parameters within a body cavity of a patient. More particularly, the present invention is directed to a self-powered interface circuit for safely interfacing a transducer sensor to a patient vital signs monitor.

2. Background Information

In many medical procedures, medical personnel need to monitor various physiological conditions that are present within a body cavity of a patient. These physiological conditions are typically physical in nature—such as pressure, temperature, rate-of-fluid flow—and provide the physician or medical technician with critical information as to the status of a patient's condition. Obviously, the manner by which these types of parameters are measured and monitored must be safe, accurate and reliable.

One device that is widely used to monitor such conditions is the blood pressure transducer. A blood pressure transducer senses the magnitude of a patient's blood pressure, and converts it into a representative electrical signal. This electrical signal is then supplied to a vital signs monitor that displays, records or otherwise monitors the magnitude of the patient's blood pressure.

Traditionally, a blood pressure transducer has consisted of a pressure responsive diaphragm that is mechanically coupled to piezoresistive elements connected in a Wheatstone Bridge-type circuit arrangement. When the diaphragm is placed in fluid communication with a body cavity (such as within the arterial or venous system), pressure induced deflections of the diaphragm cause the resistive elements to be stretched (or compressed, depending on their orientation). According to well-known principles, this alters the resistance of the elements in a manner that is proportional to the applied pressure. The magnitude of the applied pressure can thus be detected by applying an excitation power signal (usually in the form of a voltage) to the inputs of the Wheatstone bridge circuit, and by simultaneously monitoring the bridge output signal. The magnitude of that signal reflects the amount by which the bridge resistance has changed, according to Ohm's law.

Typically, an electrical cable connects the Wheatstone bridge portion of the transducer sensor to a transducer amplifier circuit contained within the vital signs monitor. This amplifier circuit supplies the excitation power signal to the Wheatstone bridge, and simultaneously monitors the bridge output signal. The excitation power signal is typically in the form of a voltage and, depending on the monitor type and manufacturer, can have varying magnitudes and formats, both time-varying (sinusoidal, square-waved and pulsed) and time independent (DC).

According to the principles under which conventional Wheatstone bridge transducers operate, transducer amplifier circuits in most patient monitors have been designed to expect a sensor output signal having a magnitude that is proportional to the magnitude of the excitation power signal and also proportional to the magnitude of the sensed pressure. Because different monitors supply excitation power signals having different magnitudes and/or frequencies, standard proportionality constants have been developed. These proportionality standards allow any sensor to be readily adapted for use with any patient monitor also calibrated to adhere to the proportionality standard.

Several benefits are provided by this compatibility. Blood pressure transducers could be used interchangeably with patient monitors from different manufacturers. As such, medical personnel were not required to select a specific transducer for use with a specific monitor. Further, hospital investments in preexisting patient monitors were preserved, thereby reducing costs. As a consequence, vital signs monitors adhering to these proportionality standards have achieved almost universal acceptance in medical environments.

However, the blood pressure transducers and monitors that have been previously used, and the resulting standards that have evolved, are not without drawbacks. For instance, the sensors used in these systems were typically positioned external to the patient's body and placed in fluid communication with the body cavity via a fluid-filled catheter line. Pressure variations within the body cavity are then indirectly communicated to the diaphragm by way of fluid contained with the catheter line. As such, the accuracy of such systems has suffered due to variations in hydrostatic pressure and other inconsistencies associated with the fluid column.

In response to this problem, miniaturized sensors using advanced semiconductor technologies have been developed. These types of transducer sensors are extremely accurate, inexpensive and still utilize the well known Wheatstone bridge-type of circuit arrangement, which is typically fabricated directly on a silicone diaphragm. Further, the sensors are sufficiently small such that they can actually be placed on the tip of an indwelling catheter and reside directly within the arteries, tissues or organs of the patient. This eliminates the need for a fluid line because the fluid pressure is communicated directly to the transducer diaphragm. As a result, these sensors—often referred to as an indwelling or catheter-tipped transducers—provide a much more accurate measurement of the patient's blood pressure.

Unfortunately, the electrical configurations of these miniaturized semiconductor sensors are not always compatible with the transducer amplifiers in existing patient monitors. For instance, the miniaturized sensors often cannot operate over the entire range of excitation signal magnitudes and frequencies found among the various types of patient monitors. Thus, they cannot be connected directly to many of the patient monitors already in use. To be used with such existing monitors, a specialized interface must be placed between the sensor and the monitor. Such an arrangement necessitates additional circuitry on the interface and, because existing monitors have been designed to provide only limited amounts of power, the additional circuitry may require an independent source of electrical power. As a consequence, use of the newer miniaturized sensors often add cost and complexity to the overall system.

In addition, because of the above limitations, these sensors must often be configured to generate an output signal which is proportional to the pressure sensed, but that is not proportional to the excitation signal supplied to the sensor by the monitor. As discussed, this does not conform with the electrical format required by the many monitors that are commercially available and already in widespread use. As such, the newer sensors can only be used with specific monitor types, thereby requiring additional, and often redundant, equipment to be purchased. This is especially undesirable given the cost sensitivities so prevalent in today's health care environment.

Use of the newer, more miniaturized sensors has raised additional problems as well. When an electrically conductive device such as a semiconductor pressure transducer is connected both to a patient (either directly or via a patient fluid line) and to an electronic monitoring instrument, great care must be taken to insure that electrical currents at standard power line frequencies cannot flow from the patient, through the transducer connection, and to ground. Such currents are known to cause patient injury even when they only appear at micro-ampere levels.

An additional risk occurs in patients which are undergoing defibrillation while having an electrically conductive transducer attached. In this case, the transducer must not only prevent currents from flowing through the transducer connection, but it must also maintain this protection up to an electrical potential of approximately 5 KV which might appear between the patient and the earth ground connection of the monitor. Industry standards have been established which require the transducer to provide this electrical protection.

In the past, Wheatstone bridge-type transducers that connect to the patient via a fluid-line are sufficiently large such that electrical protection could be provided with an insulating silicone barrier. This mechanical barrier is placed directly between the electrically conductive elements on the transducer diaphragm and the fluid-line, thereby providing a electrical isolation between the patient and the monitor. Unfortunately, this barrier can further affect the accuracy of the transducer, and adds complexity and cost to the device.

Due to the extremely small sizes of the newer semiconductor sensors previously discussed, electrical isolation provided with such a mechanical means is not practical— especially when the sensor is placed on a catheter tip. To now, the problem of providing electrical isolation between the transducer has been solved by using fiber-optics. A fiber-optic transducer senses pressure by the modulation of a light signal and thereby eliminates the need for an electrical connection between the patient and the monitor. Although this approach solves the electrical isolation problem, fiber-optic transducers are expensive, subject to calibration problems and long term drift, require complex circuitry to operate and interface with existing patient monitors, and are difficult to manufacture.

In contrast, the newer semiconductor pressure transducers are extremely suitable for use as catheter tip transducers in that they: are inexpensive and easy to manufacture; are easy to calibrate; are very accurate and not subject to long term drift; and still utilize the well-known and proven Wheatstone bridge-type circuit arrangement.

Consequently, there is a need for an arrangement that insures that a miniaturized semiconductor sensor is electrically compatible with a patient monitor. Such an interface arrangement needs to be inexpensive, easy to use and capable of being used with any one of a number of preexisting monitor types. Further, the interface should be capable of deriving all of its electrical power from the excitation power signal provided by the monitor. Finally, if needed, the interface must also provide adequate electrical isolation between the patient and the patient monitor.

OBJECTS AND BRIEF SUMMARY OF THE INVENTION

The present invention has been developed in response to the present state of the art, and in particular, in response to these and other problems and needs that have not been fully or completely solved by currently available solutions for connecting and electrically interfacing an electrical sensor to patient monitors. It is therefore a primary object of the present invention to provide a novel interface circuit that physically interconnects and electrically interfaces a semiconductor transducer sensor with an existing patient monitor.

Another object of the present invention is to provide an interface circuit that generates a suitable sensor excitation signal and derives its sole source of electrical power all from the single monitor excitation signal provided by the patient monitor.

Yet another object of the present invention is to provide an interface circuit that is able to derive a correct level of electrical power from any one of a number of different monitor excitation signal formats, including varying frequencies and magnitudes.

A related object of the present invention is to provide an interface circuit that is able to interface a semiconductor transducer sensor with a variety of different types of patient monitors.

Another object of the present invention is to provide an interface circuit that does not unduly load or distort the monitor excitation signal waveform that is provided by the patient monitor.

Still another object of the present invention is to provide an interface circuit that electrically isolates the sensor from the patient monitor.

Another object of the present invention is to provide an interface circuit that provides a response signal to the patient monitor that is proportional both to the magnitude of the monitor excitation signal and to the magnitude of the pressure detected by the sensor, thereby simulating a standard Wheatstone bridge-type transducer response.

These and other objects and features of the present invention will become more fully apparent from the following description and appended claims, or may be learned by the practice of the invention as set forth hereinafter.

Briefly summarized, the foregoing and other objects are achieved with a novel interface circuit for connecting and interfacing a physiological sensor, such as a semiconductor blood pressure transducer, to a patient monitor. Importantly, the interface circuit is adapted for use with any patient monitor that provides an excitation power signal, regardless of the magnitude and/or time varying format of that signal. As such, the interface can be used with any one of the many patient monitors commercially available and already used in most hospitals.

In one embodiment of the invention, the interface circuit is connected, via a detachable electrical cable, to the patient monitor that is supplying the excitation power signal, which is typically in the form of a voltage. From that excitation signal, a power supply means derives the sole electrical power for the interface circuit, as well as a suitable excitation signal for the sensor. Preferably, the electrical power generated is comprised of at least one unregulated power supply voltage, which has a magnitude that is directly proportional to the excitation power signal supplied by the monitor, and a regulated power supply voltage. These voltages can be used to power the electrical components (both analog or digital) used on the interface circuit.

In another aspect of the invention, the interface circuit further includes, again by way of a detachable cable, a means for receiving the sensor output signal that is generated by the transducer sensor in response to the sensor excitation signal. This receiving means provides a response signal that is proportional only to the magnitude of the pressure (or similar physiological parameter) sensed by the transducer, and which is not proportional to the magnitude of the excitation power signal.

A scaling means receives the response signal, and functions so as to provide a parameter signal which has a magnitude that is proportional to the magnitude of the pressure being sensed by the transducer, and that is also proportional to the magnitude of the excitation power signal being supplied by the patient monitor. This parameter signal thus simulates a standard Wheatstone bridge pressure transducer response, and is in the electrical format expected by most patient monitors. The interface circuit can further include an attenuation means for attenuating the parameter signal to a predetermined nominal scale factor which corresponds to a particular type of Wheatstone bridge transducer.

When used in conjunction with a catheter tip transducer, or in any other environment where electrical isolation is required, the interface circuit of the present invention provides complete electrical isolation between the semiconductor sensor and the vital signs monitor. In this embodiment, the power supply means includes a means for electrically isolating the sensor excitation signal from the excitation power signal supplied by the monitor. This prevents any hazardous leakage currents from flowing between the monitor and the patient via the interface circuit. Similarly, the receiving means portion of the circuit includes a means for electrically isolating the sensor output signal from the simulated sensor signal that is supplied back to the monitor. In this way, defibrillation potentials that are applied to the patient cannot flow to and damage the monitor.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not to be considered to be limiting of its scope, the invention in its presently understood best mode will be described and explained with additional specificity and detail through the use of the accompanying drawings in which.

DETAILED DESCRIPTION OF THE PREFERRED EMBODIMENTS

Figure 1:
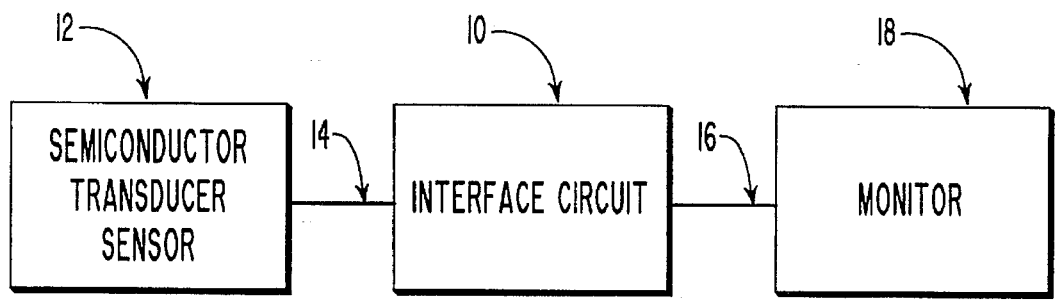
FIG. 1 is a block diagram illustrating generally the manner by which the interface circuit of the present invention electrically interconnects and interfaces a Wheatstone bridge-type sensor device to a patient monitor.

Referring first to FIG. 1, the interface circuit of the present invention, designated generally at 10, is used generally in conjunction with a system for measuring a physiological condition within a body cavity. Physiological conditions can include, for example, temperature, blood gas levels, hematocrit levels and blood pressure. In the illustrated embodiment, the physiological condition that is monitored is the blood pressure present within a patient's arterial or venous system. However, it will be appreciated that the present invention can also be used in systems measuring other physiological conditions.

As is well known, a conventional vital signs monitor is typically electrically connected directly to a standard strain gauge transducer. The monitor then supplies an excitation power signal to the inputs of a Wheatstone bridge strain gauge formed on the diaphragm of the transducer. The conventional monitor simultaneously monitors the magnitude of the output signal present at the Wheatstone bridge outputs. Most monitors are designed to comply with industry-wide standards, and therefore require that this output signal be proportional both to the magnitude of the excitation power signal and to the magnitude of the sensed pressure (or similar physiological parameter). In this way, the vital signs monitor, such as monitor 18, can use a predetermined scale factor to convert the output signal into a corresponding pressure value. The monitor then displays, records or otherwise monitors that value.

Recently, advanced fabrication techniques have resulted in newer electronic sensors that are much smaller, more accurate, and that require less operating power than previous strain gauge transducers. Although these miniaturized sensors, such as the semiconductor transducer sensor 12 illustrated in FIG. 1, still utilize a standard Wheatstone bridge-type circuit arrangement, they are configured so as to be not electrically compatible with many existing monitors. More specifically, such sensors typically require an electrical excitation signal that has a specific magnitude and/or frequency that often differs from earlier sensors and that is not provided by conventional monitors. Further, these sensors often do not generate an output signal that complies with the standard electrical format expected by the monitor's electronics. However, because the medical industry has made a significant investment in the conventional monitors, it is desirable to utilize the newer sensors, such as transducer 12, with the conventional monitor 18. As FIG. 1 illustrates, this function, described in further detail below, is provided by interface circuit 10.

In addition to providing a suitable electrical interface, there is often a need to provide complete electrical isolation between the electrical transducer 12 and the monitor 18. As previously discussed, such isolation is needed to protect the patient from dangerous monitor leakage currents, and to protect the monitor from the high voltages often present during patient defibrillation. Thus, electrical isolation is required whenever the electrical sensor is placed in electrical contact with the patient, either directly or indirectly. Often, such isolation cannot be practically provided by way of a non-conductive mechanical barrier. Again, this function is also provided by the interface circuit 10.

With continued reference to FIG. 1, it is shown how the semiconductor transducer sensor 12 electrically connected to the interface circuit 10 by way of a sensor cable 14. Also connected to the interface circuit 10, via a monitor cable 16, is the conventional vital signs monitor, designated at 18.

Figure 1A:
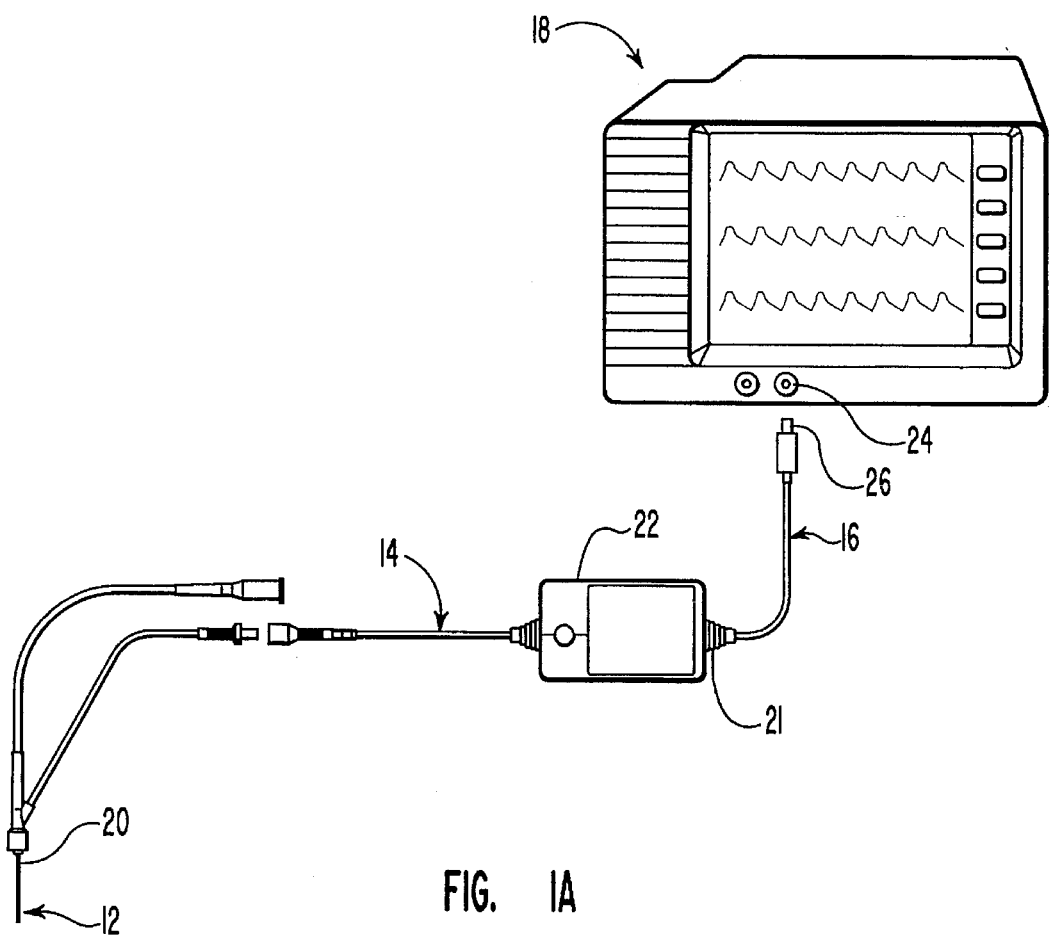
FIG. 1A is a perspective view of one embodiment of the present invention wherein the interface circuit is used to interconnect a vital signs patient monitor with a catheter tip sensor.

FIG. 1A illustrates in further detail one example of a system shown generally in FIG. 1. Here, transducer 12 is placed at the tip of an indwelling catheter 20. In use, the catheter tip and the transducer 12 are placed in direct fluid communication with the patient's arterial or venous system (not shown). It will be appreciated that in the alternative, the semiconductor transducer 12 could be placed externally to the patient and placed in fluid communication with the patient's blood indirectly, as for example, by way of a standard catheter fluid-line. In either case, the semiconductor transducer 12 cannot be connected directly to monitor 18 because of the electrical incompatibilities noted above.

With continued reference to FIG. 1A, the sensor cable 14 is used to electrically connect transducer 12 to the interface circuit 10, which is housed within module 22. Similarly, interface circuit 10 is electrically connected to monitor 18 by way of monitor cable 16. In the preferred embodiment, a connector 48 (discussed below) is formed on the interface circuit 10 so as to detachably receive an electrical plug 21 formed on one end of the monitor cable 16. Formed on the opposite end of cable 16 is another plug 26, which is detachably received within a standard receptacle 24 located on monitor 18.

Figure 2:
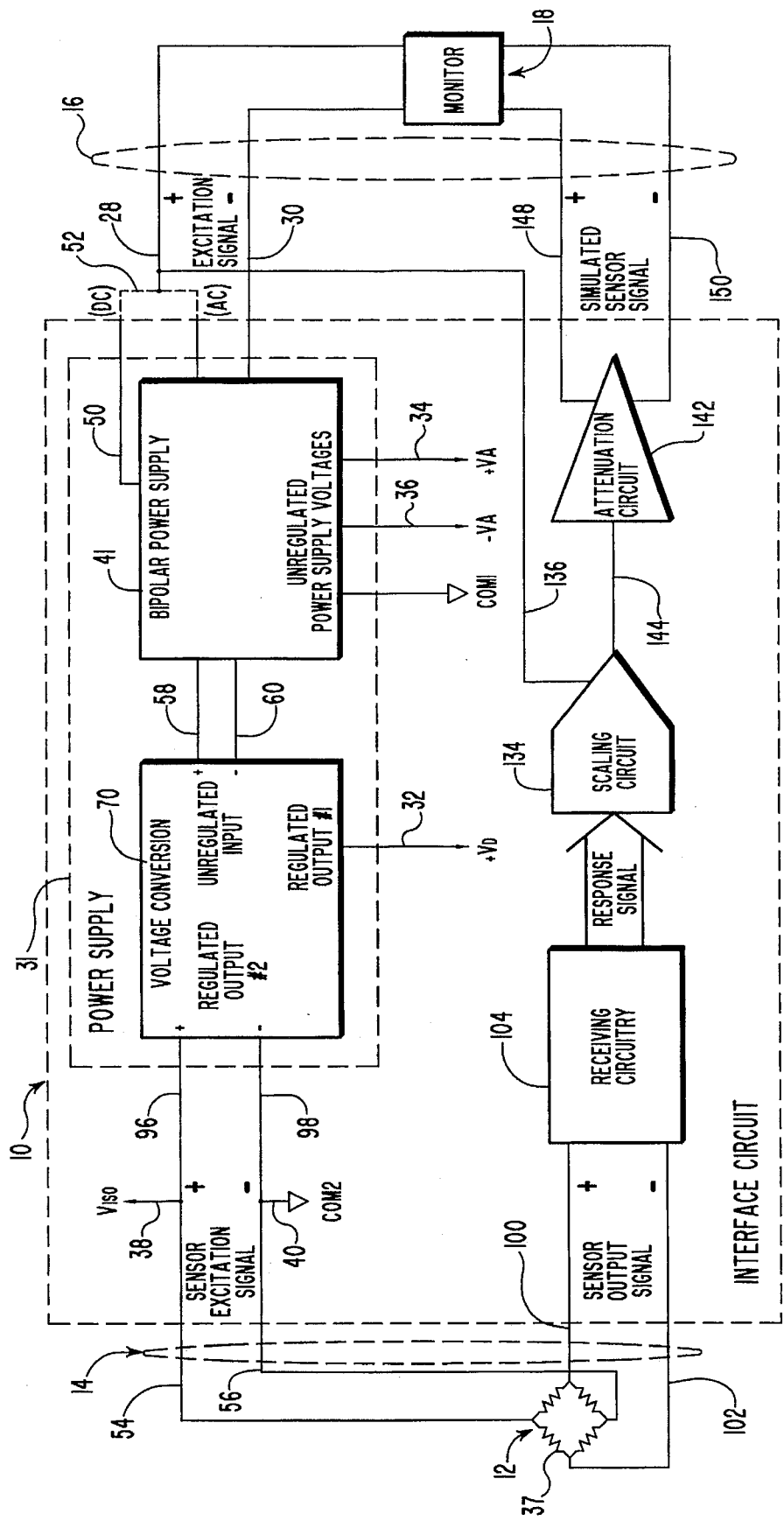
FIG. 2 is a block diagram illustrating in further detail the components which make up one embodiment of the interface circuit of the present invention.

Referring now to FIG. 2, illustrated in block diagram form is one presently preferred embodiment of the interface circuit 10. As is shown, the patient vital signs monitor 18, which acts as an excitation signal source, is electrically connected to the interface circuit 10 by a four-wire monitor cable 16. Also connected to the interface circuit 10, by way of a four-wire sensor cable 14, is semiconductor transducer 12 having a Wheatstone bridge-type circuit 37.

Monitor 18 contains standard transducer amplifier circuitry (not shown) which generates an excitation power signal, typically in the form of an excitation voltage. Two of the cable 16 wires, a positive 28 and a negative 30 excitation signal line, carry this excitation voltage from monitor 18 to the interface circuit 10. Depending on the type of monitor being used, the format of excitation voltage can vary widely. Typically, it is anywhere in the range of four (4) to ten (10) volts RMS, and may vary in frequency from D.C. to 5 kHz.

With continued reference to FIG. 2, interface circuit 10 comprises a power supply means for receiving the excitation voltage signal from monitor 18. From this excitation voltage signal, the power supply means derives at least one supply voltage for use as the sole source of electrical power for the interface circuit 10. The power supply means also functions to generate, from the excitation voltage signal, a sensor excitation signal that is in a suitable electrical form, which is supplied to the Wheatstone bridge 37 portion of semiconductor transducer 12.

Thus, the operating power for the electrical components used in the interface circuit, as well as a suitable sensor excitation signal for the sensor device 12, are derived solely from the excitation signal that is supplied by monitor 18. This is accomplished regardless of the format of the excitation signal supplied by monitor 18, thereby allowing interface circuit 10 to be used with different types of monitors. Advantageously, this capability eliminates the need for a separate power supply, thereby reducing the physical space required by interface circuit 10, as well as its overall cost.

By way of example and not limitation, the supply voltage derived by power supply means preferably includes three separate voltages: a fixed voltage $V_D$ shown at line 32, and two unregulated supply voltages $+V_A$ and $-V_A$ shown at lines 34 and 36 respectively. Further, the sensor excitation signal is shown as preferably comprising a regulated voltage (although it could also be supplied as a current), and is illustrated as comprising a voltage $V_{ISO}$ 38, present between schematic lines 96 and 98.

In a preferred embodiment, the power supply means is comprised of a bipolar supply means and a voltage conversion means. The bipolar supply means receives the excitation signal generated by monitor 18, and is that portion of the power supply means that generates a positive and a negative unregulated power supply voltage, $+V_A$ and $-V_A$ (shown at lines 34 and 36 respectively). Importantly, $+V_A$ and $-V_A$ are DC voltages, and have magnitudes which are equal, but opposite in polarity. Further, the magnitudes of $+V_A$ and $-V_A$ are both directly proportional to the magnitude of the incoming excitation signal supplied by monitor 18.

The voltage conversion means functions so as to receive the positive unregulated power supply voltage $+V_A$, and then generate therefrom both the fixed output voltage $+V_D$ (shown at 32), and the fixed regulated sensor excitation voltage $V_{ISO}$ (shown at 38). Regulated sensor excitation voltage $V_{ISO}$ is then supplied to the inputs of the Wheatstone bridge 37 via a positive sensor signal excitation line 54 and a negative sensor signal excitation line 56 portion of the sensor cable 14.

Figure 3:
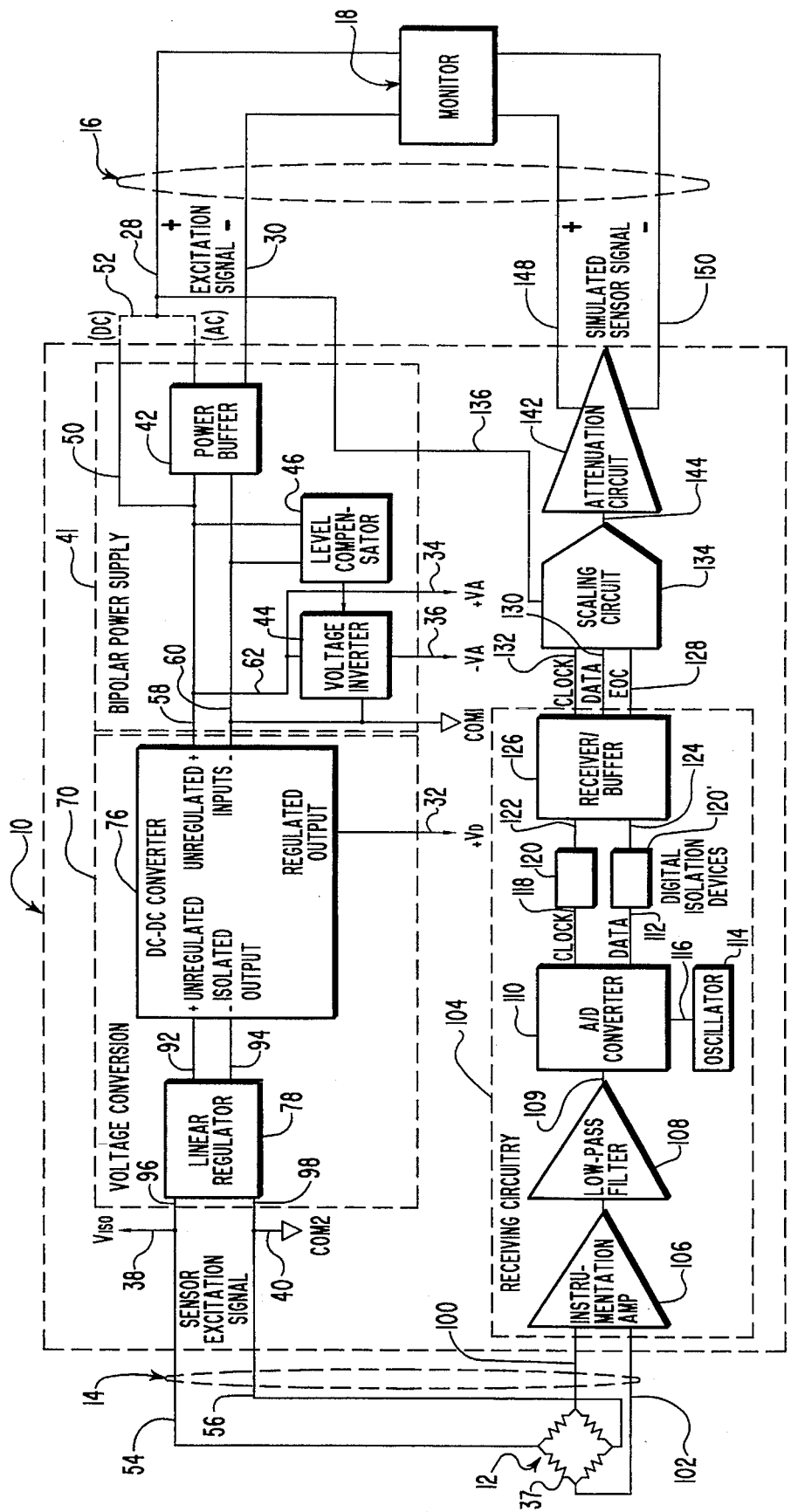
FIG. 3 is a block diagram illustrating in further detail the interface circuit.

By way of example and not limitation, FIG. 2 illustrates how in one presently preferred embodiment, the bipolar supply means portion of the power means comprises a bipolar power supply circuit 41. FIG. 3 illustrates the bipolar power supply circuit 41 as comprising, for example, a power buffer circuit 42, a voltage inverter 44 and a level compensator circuit 46, each of which is illustrated in further detail in FIG. 4, to which reference is now made.

Figure 4:
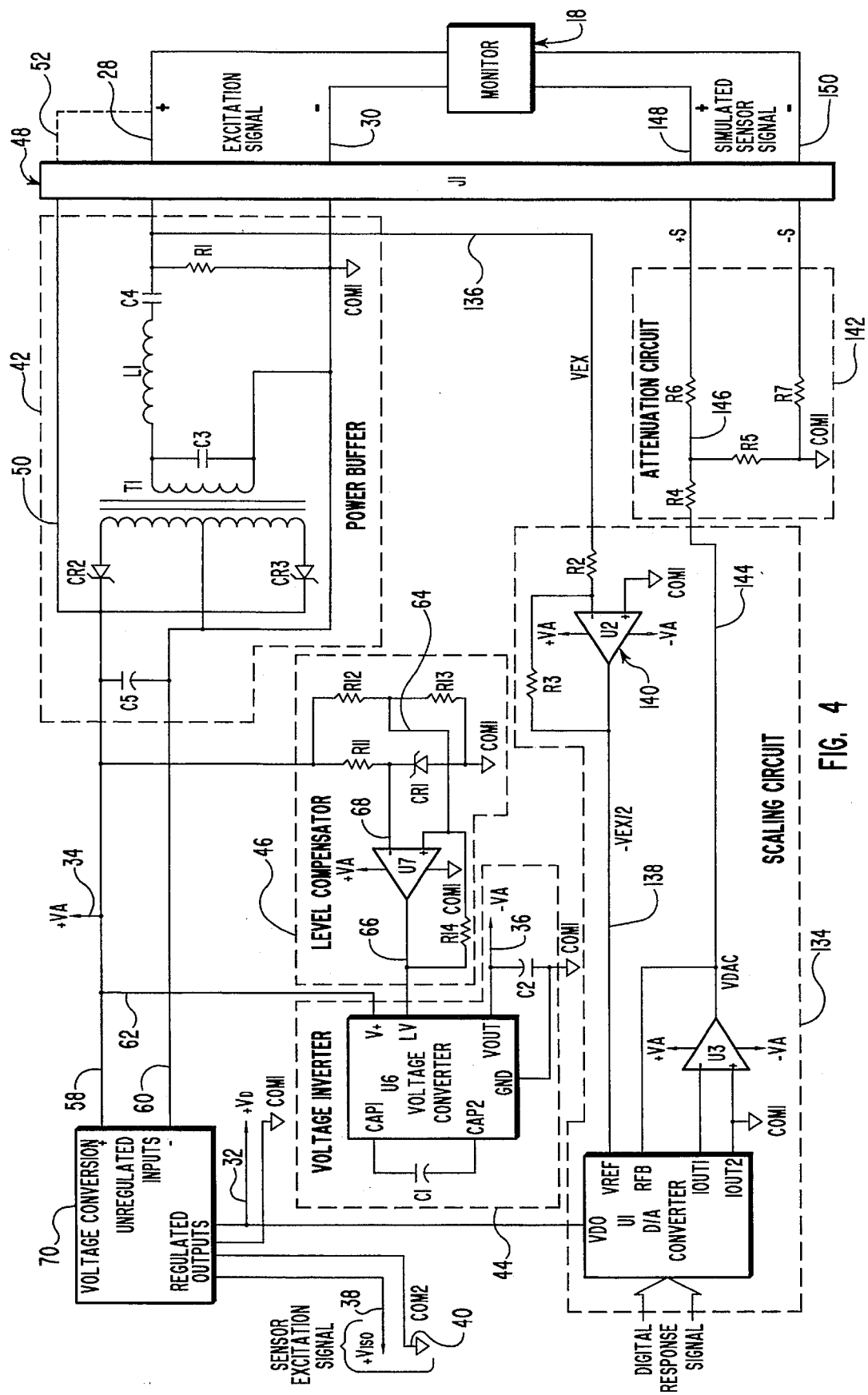
FIG. 4 is an electrical schematic illustrating in further detail portions of the interface circuit of the present invention.

Power buffer circuit 42 connects directly to the positive and negative excitation signal lines 28, 30, by way of a standard electrical connector J1, generally designated at 48, and consists of the following elements: resistor R1, capacitors C3, C4 and C5; inductor L1; diodes CR2 and CR3; and transformer T1; all of which are connected in the circuit configuration shown in FIG. 4.

In the preferred embodiment, power buffer circuit 42 also includes a bypass means for operating the interface circuit 10 in either a AC operating mode, or in a DC bypass operating mode. The bypass means comprises, for example, a single bypass wire 50 connected to detachable connector J1 as a separate signal output. If monitor 18 is of a type that provides an excitation signal voltage that is DC only, the monitor cable 16 will include a separate jumper wire 52 which will interconnect the positive excitation signal line 28 with the bypass wire 50 when the cable 16 is received within the connector J1. This causes the positive excitation signal line 28 to be electrically connected directly to the cathode of diode CR2, thereby causing that portion of the excitation signal to bypass portions of the power buffer circuit 42.

Because the jumper wire 50 is brought out to the connector J1 as a separate signal, this bypassing can be accomplished by merely including the jumper wire 52 within the electrical monitor cable 16. Alternatively, the monitor cable 16 can be equipped with a monitor cable connector (not shown) which can include the necessary jumper wire 52. In either case, the monitor cable connector/monitor cable is specific to the model of monitor 18 being used. Importantly, no changes need to be made to the interface circuit 10, which can be used interchangeably with monitors providing either DC or AC excitation voltages.

As can be seen in FIG. 4, when configured in a DC bypass mode, capacitor C4 and diodes CR2 and CR3 act as open circuits, thereby preventing the other components within the power buffer circuit 42 from loading, and thereby distorting, the DC excitation voltage signal. Capacitor C5 merely acts as a simple filter on the DC excitation voltage signal.

In contrast, when the excitation voltage signal supplied by monitor 18 is AC, the monitor cable 16 will not be equipped with a jumper wire 52. As such, the transformer T1 and diodes CR2, CR3 portion of the power buffer circuit 42 together function as a full wave rectifier on the AC excitation voltage signal. To filter the ripple from the signal received from the full wave rectifier, capacitor C5 is connected across the positive 58 and negative 60 outputs of the power buffer circuit 42.

Transformer T1 further acts to isolate the rectified signal (shown as $V_A$ at the positive output 58 of the power buffer circuit 42) from the excitation voltage signal received from monitor 18. This enables the negative output 60 of the power buffer circuit 42 to be connected directly to the negative excitation signal line 30. This negative output 60 acts as the first electrical common, referred to as COM1, for the interface circuit 10. As a result, the interface circuit 10 requires no electrical reference to earth ground, and is unaffected by the nature of the electrical reference of monitor 18.

With continued reference to FIG. 4, it will be appreciated that the full-wave rectifier portion of the power buffer circuit 42 would ordinarily present an electrical load to an AC excitation voltage signal which is neither continuous nor resistive in nature. In contrast, the transducer amplifiers (not shown) used in most patient monitors are designed to power a Wheatstone Bridge transducer directly, which presents a continuous and resistive load and does not induce any severe distortion on the excitation voltage signal. Thus, to work properly with such monitors, the interface circuit 10 must simulate the simple resistive impedance presented by a standard Wheatstone bridge transducer and thereby minimize any excessive distortion of the excitation voltage signal. To do so, the power buffer circuit 42 preferably comprises an AC power filter means for preventing the excitation voltage signal from being distorted.

By way of example and not limitation, FIG. 4 illustrates one preferred embodiment of the AC power filter means as comprising capacitors C3 and C4, and inductor L1. These components are arranged such that, together with the internal inductance, capacitance and resistance of the windings of transformer T1, they form an AC power filter that presents a complex impedance to the excitation voltage signal. This complex impedance is primarily resistive in nature, and thus simulates the impedance of a Wheatstone bridge transducer. The respective component values will depend highly on the frequency of the excitation voltage signal, and thus may vary depending on the type of monitor 18 being used.

As is shown in FIGS. 3 and 4, the positive and negative outputs 58, 60 of the power buffer circuit 42 define the electrical signal known as the positive unregulated power supply voltage $+V_A$ (shown at 34), which has only a DC component. Importantly, the magnitude of $+V_A$ is proportional to the magnitude of the excitation voltage supplied by monitor 18. Specifically, the magnitude of $+V_A$ is equal (i.e., exactly proportionate) to that of the excitation voltage when the interface circuit is operated in a DC bypass mode, and it will be directly proportional, but not equal, to the AC RMS value of the excitation voltage when operated in AC mode. This voltage thus provides an ideal source of electrical power for other components (especially analog components) within the interface circuit 10.

The $V_A$ signal is electrically connected, as is shown at schematic line 62, to the voltage inverter circuit 44. The voltage inverter circuit functions so as to generate a negative tracking power supply voltage $-V_A$, which has a magnitude that is very close to the magnitude of $V_A$, but of opposite polarity. In a preferred embodiment, voltage inverter circuit 44 is comprised of a voltage converter U6 and capacitors C1 and C2, connected as shown. The voltage converter U6 illustrated is known as an ICL 7662 CMOS voltage converter, and is available from numerous integrated circuit manufacturers. It will be appreciated that other voltage converters, and/or circuit arrangements could be used to provide the same function, and still fall within the intended scope of the invention.

As noted above, depending on the type of vital signs monitor 18 being used, the excitation voltage signal can be one of several different magnitudes. Voltage converters of the type used in the preferred embodiment have a low voltage and a high voltage operating mode, which must be selected depending on the value of the input voltage $V_A$. Specifically, when $V_A$ falls below a threshold voltage, the LV input to voltage converter U6 must be connected to the first electrical common COM1 through a low impedance. When $V_A$ is above the threshold level, the connection between LV and COM1 must be opened. Thus, the preferred embodiment includes a level compensator circuit 46, which monitors the magnitude of $V_A$ and, based on that value, automatically configures the LV input of voltage converter U6 to the appropriate level.

FIG. 4 illustrates, by way of example and not limitation, that a preferred circuit configuration for the level compensator circuit 46 comprises a comparator U7; resistors R11, R12, R13 and R14; and reference diode CR1. Resistor R11 and reference diode CR1 are connected between the positive and negative buffer outputs 58, 60 to establish a fixed reference voltage 68 at the cathode of CR1. This fixed reference voltage (at 68) is then connected to an input of comparator U7. Resistors R12 and R13 are connected as a first voltage divider, with a first divider output connected to the other input of comparator U7, as is shown at schematic line 64. The output of comparator U7 is connected to the LV input of voltage converter U6, schematically shown at line 66. Resistor R14 provides hysteresis for the comparator U7.

In operation, the values of resistors R12 and R13 are chosen so that the first divider output 64 will be equal to the fixed reference voltage 68 when the magnitude of the positive unregulated power supply voltage $V_A$ equals the threshold voltage of the voltage converter U6. When the magnitude of $V_A$ is less than the threshold voltage, the comparator U7 output is internally shorted to the first electrical common COM1. When the magnitude of $V_A$ is greater than the threshold voltage, the comparator U7 output is not connected to COM1. In this way, the proper configuration of the LV input to voltage converter U6 is maintained, and the interface circuit 10 can thus be used over an extended range of excitation voltages without any need for user adjustment.

The above described circuitry provides a bipolar power supply consisting of the positive unregulated power supply voltage $+V_A$ and the negative tracking power supply voltage $-V_A$. Because these voltages are unregulated, but proportional to the incoming excitation voltage, the requisite amounts of electrical power are efficiently provided to analog components within the interface circuit 10 without overly loading the excitation voltage.

In addition to providing electrical power to the interface circuit's analog circuitry, electrical power for any components requiring a regulated power supply voltage is also generated in the preferred embodiment. This function is provided by the voltage conversion means portion of the power supply means, which also functions to provide the requisite sensor excitation voltage.

Referring again to FIG. 2, an example of the voltage conversion means is shown as comprising a voltage conversion circuit 70, which is electrically connected to the bipolar power supply circuit 41. The voltage conversion circuit 70 has a first regulated output corresponding to fixed voltage $V_D$ (shown at 32), and a second regulated output corresponding to fixed voltage $V_{ISO}$ (shown at 38). Preferably, $V_D$ has a fixed magnitude of approximately 5 volts DC, and can thereby be used to power standard digital circuitry.

As is further shown in FIG. 3, the voltage conversion circuit 70 is preferably comprised of a DC—DC converter circuit 76 and a linear regulator circuit 78. The positive ($V_A$) and negative (COM1) buffer outputs 58, 60 are connected directly to the unregulated inputs of the DC—DC converter circuit 70, which then generates a regulated output corresponding to $+V_D$, and a positive 92 and negative 94 unregulated output. The positive 92 and negative 94 unregulated output is connected to the linear regulator circuit 78. Importantly, the first regulated output $V_D$ is maintained constant even while the voltage magnitude at the unregulated inputs 58, 60 is allowed to fluctuate to values both less than or greater than the desired value of $V_D$.

Figure 5:
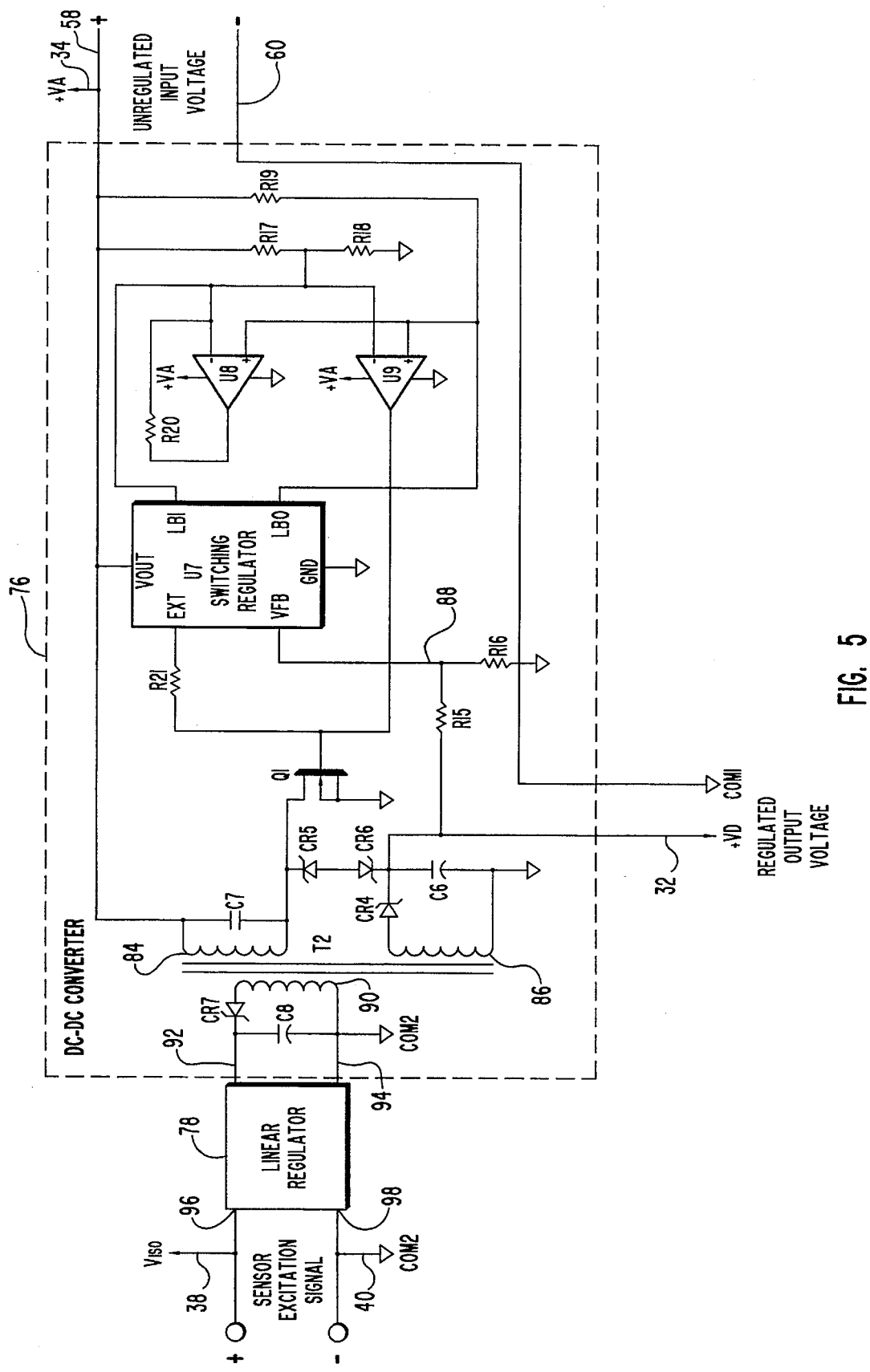
FIG. 5 is an electrical schematic illustrating in further detail the circuitry making up the DC—DC converter portion of the interface circuit.

By way of example and not limitation, FIG. 5 illustrates a preferred embodiment of the DC—DC converter circuit 76. Included in circuit 76 is a switching regulator U7, which in the preferred embodiment is a MAX643 adjustable output switching regulator controller manufactured by Maxim Integrated Products. It will be appreciated that numerous other switching regulator controller circuits are known and could also be used. Regulator U7 is powered by the positive unregulated power supply voltage $+V_A$, which is connected across pins VOUT and GND as shown. Output EXT of regulator U7 is connected through resistor R21 to transistor Q1. When the EXT output of U7 cycles on and off, transistor Q1 cycles on and off, and a first alternating current flows through a primary winding 84 of transformer T2, thereby generating a magnetic flux in the core of the transformer T2. This magnetic flux in turn generates a second alternating current in a first secondary winding 86 of transformer T2, which is then rectified by diode CR4 and capacitor C6. The junction between the cathode of diode CR4 and capacitor C6 corresponds to the first regulated output $V_D$ (shown at 32) of the voltage conversion circuit 76.

Resistors R15 and R16 make up a second voltage divider that is connected across the first regulated output 32 and the first electrical common COM1. The second voltage divider has an output 88 connected to a VFB input of regulator U7. The regulator U7 controls the duty cycle of the on-off switching of the EXT output in response to the voltage at the VFB input, thereby regulating the voltage at the first regulated output $V_D$.

Capacitor C7 and diodes CR5 and CR6 act as a clamp circuit, limiting the voltage at the junction of Q1, C7, CR5 and the primary winding 84 during times when Q1 is turned off. Comparators U8 and U9, and resistors R17, R18, R19 and R20 act together with an LBI input and an LBO output of regulator U7 as an undervoltage shutdown circuit. This shutdown circuit acts to force the transistor Q1 to be shut off at all times when the positive unregulated voltage $V_A$ falls below a value which is too low for the DC—DC converter circuit 76 to maintain the desired voltage at the first regulated output 72 ($V_D$).

FIG. 5 also illustrates how in one preferred embodiment, the DC—DC converter circuit 76 includes means for electrically isolating the sensor excitation signal from the excitation power signal supplied by the monitor 18. By way of example and not limitation, this electrical isolation means is comprised of a second secondary winding 90 formed on the transformer T2, which generates a third alternating current that is rectified by diode CR7 and capacitor C8. This produces the unregulated output voltage between schematic lines 92 and 94, having an isolated common shown as COM2. Importantly, this output voltage is galvanically isolated from all other circuits within the DC—DC converter circuit 76, and can thus be used to provide a completely isolated sensor excitation signal to the pressure transducer 12, and to any other components on the interface circuit 10 which are electrically connected to pressure transducer 12. This capability is important for those applications where electrical isolation is required between that part of the circuitry which connects directly to the monitor 18 and that part of the circuitry which connects to the transducer 12, such as would be the case with a catheter tip transducer (FIG. 1A).

As is further shown in FIG. 5, the isolated output voltage between schematic lines 92 and 94 is supplied to a linear regulator 78. In one preferred embodiment, this regulator 78 is an LM2936 device manufactured by National Semiconductor, although other linear regulator circuits could be used. Linear regulator 78 provides a regulated isolated output of 5 VDC between outputs 96 (corresponding to signal $V_{ISO}$ 38) and 98 (corresponding to COM2 40). As is shown in FIGS. 2 and 3, this isolated output signal is connected to the positive 54 and negative 56 sensor signal lines in the sensor cable 14, via isolated output protection devices (not shown), where it is referred to as the sensor excitation signal. The positive and negative sensor signal lines 54, 56 are then electrically connected to the two input nodes of the Wheatstone bridge 37 portion of transducer 12.

To summarize, the power supply circuit 31 allows the interface circuit 10 to efficiently derive all of its operating power, as well as a suitable sensor excitation signal, solely from the excitation signal that is supplied by a vital signs monitor 18. Further, the power supply circuit 31 is configured such that it can operate over a wide range of excitation voltage levels, AC or DC, so that the interface circuit 10 can be used in conjunction with many different types of monitors. The power supply circuit 31 is also designed so that it simulates the simple resistive impedance of a standard Wheatstone bridge-type circuit, and therefor does not induce significant waveform distortion on AC excitation voltage signals. Importantly, the power supply aspect of the interface circuit 10 provides these improvements, and yet still can be configured such that there is complete electrical isolation between that part of the circuitry which connects directly to the monitor, and that part of the circuitry which connects to the transducer. Thus, the interface circuit can safely be used in conjunction with electronic transducers that are in electrical contact with a patient.

Referring again to FIG. 2, another aspect of the present invention is shown. As is shown, the two output nodes of the Wheatstone bridge 37 portion of transducer 12 are electrically connected to the positive 100 and the negative 102 sensor output lines present within the sensor cable 14. In response to the sensor excitation signal, the Wheatstone bridge will generate across these two lines 100, 102 a sensor output signal voltage. This output signal has a magnitude that is directly proportional to the magnitude of the applied fluid pressure on transducer 12. However, the sensor output signal is not proportional to the excitation signal originally supplied by the monitor 18, and it is thus not yet in an electrical format that is compatible with monitor 18.

Interface circuit 10 includes a means for receiving this sensor output signal from sensor output lines 100 and 102 and for providing a response signal that remains proportional only to the physical parameter detected by the transducer 12. By way of example, FIG. 2 illustrates the receiving means as comprising receiving circuitry 104, which is illustrated in further detail in FIG. 3.

By way of example and not limitation, receiving circuitry 104 is comprised of: means for amplifying the sensor output signal; means for filtering high frequency components from the amplified sensor output signal; and means for converting the amplified sensor output signal to a response signal.

Referring to FIG. 3, the sensor output lines 100 and 102 are connected to the interface circuit 10 through isolated input protection devices (not shown) to means for amplifying the sensor output signal, such as an instrumentation amplifier 106. Although other similar components could be used, in the preferred embodiment the instrumentation amplifier 106 is known by the part number LT1101 and manufactured by Linear Technology Corp. The amplifier 106 is configured so as to provide a gain of 100 to the sensor output signal, although other gains could also be used.

The amplified sensor output signal is then received by a means for filtering high frequency components from the signal, such as low-pass filter circuit 108. The low-pass filter circuit 108 is designed using techniques that are well known in the art, and includes resistors, capacitors and operational amplifiers (not shown) to obtain a five-pole Butterworth filter signal response. The filter 108 is designed so that it has a cut-off frequency suitable to remove all high frequency components present in the amplified sensor output signal that would cause aliasing errors when converted to a digital format (discussed below).

The low-pass filter 108 output is electrically connected to a means for converting the sensor output signal to a response signal, which in the illustrated embodiment has a digital format. Conversion means comprises, for example, an Analog to Digital converter 110. In the preferred embodiment, the A/D converter 110 is a device known by the part number MAX189, manufactured by Maxim Integrated Products, although other equivalent devices could also be used. The A/D converter 110 sampling rate is controlled by an oscillator circuit 114 that has an oscillator output 116 with a frequency that is regulated by a crystal oscillator or ceramic resonator.

A/D converter 110 has a digital data output 112 and a clock output 118. The digital output 112 is a serial stream of data, transmitted in 12-bit segments, which digitally represents the value of the analog signal presented at the analog input 109. This signal, known as the digital response signal, represents a value that is proportional only to the magnitude of the applied pressure that is being detected by the transducer 12. The clock output signal 118 is a digital signal that is used to properly synchronize circuits which receive the digital response signal. It will be appreciated that additional digital gating and control circuits may be necessary to synchronize and properly transmit the digital response signal.

It will be appreciated that in those applications where the transducer 12 is in electrical contact with a patient, such as with a catheter tip transducer 12 shown in FIG. 1A, the transducer 12 must be electrically isolated from the monitor 18. Thus, in a preferred embodiment, the receiving circuitry 104 also includes means for electrically isolating the sensor output signal from the sensor response signal. Electrical isolation means comprises, for example, opto-isolator devices 120 and 120'. Although such devices are available from a number of manufacturers, in the preferred embodiment the opto-isolators 120, 120' are known by the part number CNW136 and manufactured by Hewlett-Packard. Other circuit arrangements are also possible, including similar opto-isolator devices, pulse transformers or isolation capacitors.

As is shown, the digital response 112 and clock 118 signals are connected to the inputs of the opto-isolators 120, 120', which then transmit the signals across an electrical isolation barrier (not shown) to the portion of the interface circuit 10 that is electrically connected to monitor 18, schematically shown at lines 122 and 124 respectively. Thus, the inputs of the opto-isolators 120, 120' are electrically connected only to the patient-side of the interface circuit 10, and the opto-isolator outputs are electrically connected only to the monitor-side of the interface circuit 10.

The outputs of the opto-isolators 120, 120' are connected to a buffer means for conditioning the electrical levels of the isolated digital response and clock signals, such as receiver/buffer circuit 126. This circuit component is well known in the art, and simply conditions and regenerates the digital response and clock signals so that they are in an electrical format that can be received by standard CMOS logic circuitry, shown at outputs 130 and 132 respectively. The receiver/buffer circuit 126 also generates an end of conversion output signal, shown at 128, which indicates the end of a 12-bit digital response signal.

It will be appreciated that although FIG. 3 denotes the use of multiple opto-isolators 120, 120', the digital response and clock signals could also be encoded into a single data line, and then transmitted across the electrical isolation barrier using a single opto-isolation device. Once received on the other side of the isolation barrier, the single data line could be decoded into separate digital response and signals. This approach is advantageous in that only one opto-isolation device would be needed, thereby reducing the amount of electrical power required by the overall interface circuit 10.

It will also be appreciated by one of skill in the art that the receiving circuitry 104 could be designed and implemented using a variety of other equivalent circuit designs. For instance, the receiving circuitry 104 could alternatively be designed using analog components. In such a design, the A/D converter 110, oscillator 114, digital isolation device(s) 120 and the receiver/buffer circuit 126 would be replaced by an analog isolation circuit and an analog recovery amplifier. Thus, the low-pass filter 108 output would be connected directly to the input of the analog isolation circuit, which would include, for instance, an analog opto-isolator such as an IL300, which is manufactured by Siemens. The analog isolation circuit may also include additional operational amplifiers, resistors and capacitors to enable the operation of the analog opto-isolator. The isolated output of the analog opto-isolator would then be connected to the inputs of an analog recovery amplifier, which conditions the electrical levels of the isolated analog response signal for use by the circuits which follow.

Whether the receiving circuitry 104 is designed using digital or analog circuit techniques, it produces a response signal that is proportional only to the magnitude of the pressure being detected by the transducer 12. As discussed, this signal is not electrically compatible with monitor 18, which expects a response signal that is proportional not only to the magnitude of the pressure, but to the excitation voltage signal simultaneously being supplied by the monitor 18. Thus, the preferred embodiment further includes a scaling means, responsive to the response signal, for providing a parameter signal that has a magnitude that is proportional to the magnitude of the excitation voltage signal and that is also proportional to the magnitude of the sensed pressure.

With reference to FIGS. 2 and 3, scaling means comprises, for example, a scaling circuit 134 which has connected at its inputs the response signal provided by the receiving circuitry 104. Also connected to the scaling circuit 134 is the positive portion of the incoming excitation voltage signal, as is shown at schematic line 136.

FIG. 4 illustrates one embodiment of the scaling circuit 134 in further detail. Here, the response signal is received from the receiving circuitry 104 described above in connection with FIG. 3, and is thus in digital form. This digital response signal is input to the digital inputs of a Digital-to-Analog converter U1, which in the preferred embodiment is a MAX543 CMOS 12-bit serial multiplying D/A converter manufactured by Maxim Integrated Products. Other equivalent D/A converters could also be used.

Connected to the voltage reference input ($V_{REF}$) of the D/A converter U1, shown as schematic line 138, is a voltage signal generated by a pre-scaling amplifier circuit, designated generally at 140. Pre-scaling amplifier circuit 140 consists of operational amplifier U2 and resistors R2 and R3, which are together connected in an inverting amplifier configuration as shown. One input of amplifier U2 is connected to the positive excitation voltage signal line 28 (via schematic line 136, denoted as voltage $V_{EX}$). The other input to amplifier U2 is connected to the first electrical common COM1. A voltage divider consisting of resistors R2 and R3 is connected as shown, wherein the value of resistor R2 is twice that of R3. Resistors R2 and R3 are also tightly matched such that the voltage produced at the output of amplifier U2 is exactly one-half the magnitude, and opposite in polarity, to the incoming excitation voltage signal (designated as $V_{EX}/2$).

This output of the pre-scaling amplifier 140 is connected (via line 138) to the $V_{REF}$ input of the D/A converter U1. D/A converter U1, responsive to the digital response signal input, then generates an analog current at its outputs (designated as $I_{OUT1}$ and $I_{OUT2}$). This current output is input to an output amplifier U3. Output amplifier U3 is powered by the positive unregulated power supply $V_A$ and the negative tracking power supply $-V_A$ voltages generated by the bipolar power supply circuit 41 described above. Due to the multiplicative operation of the D/A converter U1, the output amplifier U3 provides an analog output voltage (designated as $V_{DAC}$) having a magnitude that is proportional both to the magnitude of the sensed pressure and to the magnitude of the original excitation voltage signal supplied by the monitor. This voltage is thus in the required electrical format discussed previously, and thereby constitutes a parameter signal that can be received by monitor 18.

It will be appreciated that other equivalent circuit arrangements could be used to provide the function of scaling circuit 134. For instance, if the receiving circuitry 104 were constructed using analog circuitry, as described above, the scaling circuit 134 may include in place of the D/A converter U1 an analog multiplier circuit. The analog multiplier circuit, as for instance a transconductance multiplier, would receive the analog response signal from the receiving circuitry 104, and then generate a scaled parameter signal having a magnitude that is proportional both to the magnitude of the sensed pressure and to the magnitude of the original excitation voltage signal supplied by the monitor.

The functioning of the scaling circuit 134 also illustrates some of the advantages provided by the power supply circuit 31, and specifically the bipolar power supply circuit 41. The power supply voltages for amplifiers U2 and U3 must be larger than the largest signal anticipated at their respective outputs. However, depending on the type of monitor 18 being used, the magnitude of the excitation voltage signal supplied by monitor 18 may be as low as 2-3 volts, or as high as 15 volts. Thus, it would be impractical to anticipate the voltage required by the amplifiers U2, U3 for all monitors. Further, if a maximum voltage were selected that would work for all monitors, the interface circuit 10 would not be capable of being powered solely by the monitor excitation voltage because certain monitors operating at relatively small excitation voltages could not supply sufficient power to operate the interface circuit. But, because the amplifiers U2, U3 receive power from the bipolar power supply circuit 31 (specifically, $+V_A$ and $-V_A$), the magnitudes of which vary in proportion to the excitation voltage, the amplifiers U2, U3 can handle the full range of anticipated excitation voltages. This greatly enhances the flexibility of the interface circuit 10.

In a preferred embodiment, the interface circuit 10 further includes a means for attenuating the parameter signal to a predetermined nominal scale factor which corresponds to the particular type of transducer 12 being used. This provides a simulated sensor signal which can then be supplied back to monitor 18.

FIGS. 2 and 3 illustrate, by way of example and not limitation, one preferred embodiment of the attenuation means as comprising attenuation circuit 142, the input of which is connected to the output of scaling circuit 134, as is indicated at schematic line 144. The attenuation circuit 142 thus receives the scaled response signal provided by the scaling circuit 134, and then attenuates the signal to the nominal scale factor for standard blood pressure transducers. According to industry standards, the scale factor is typically either 5 uV/V/mm-Hg or 40 uV/V/mm-Hg, although other output scale factors could also be used. The attenuation circuit 142 also provides impedance matching, and simulates the resistive output impedance of a standard Wheatstone bridge.

FIG. 4 illustrates in further detail one manner by which the attenuation circuit 142 can be implemented. The circuit 142 includes resistors R4 and R5 which are together connected as a voltage divider, the input of which is connected to the output 144 of scaling circuit 134. Resistive values of R4 and R5 are selected such that the output of the voltage divider, indicated at 146, provides a response signal that is attenuated to one of the nominal scale factors noted above. A final positive output signal, denoted as +S, is generated by connecting the attenuated response signal to resistor R6. Similarly, a final negative output signal, denoted as −S, is provided by connected resistor R7 to the first electrical common COM1. Resistive values for R6 and R7 are selected such that together they provide impedance matching with the monitor 18 by simulating the resistive output impedance of Wheatstone bridge 37. The +S and −S signals together represent a simulated sensor signal, which is electrically connected to the monitor 18 by way of connector J1 and a positive 148 and a negative 150 line disposed within monitor cable 16.

It will be appreciated that the attenuation means could also be comprised of other equivalent circuits. For instance, rather than using a resistive network, the attenuation means could be accomplished with an inverting amplifier circuit.

Further, the simulated sensor signal (+S and −S) is referenced to the first electrical common COM1. This is virtually identical to the potential of the negative excitation line 30 (assuming that minimal current flows through resistor R7). As such, this signal is not a true Wheatstone bridge response, which typically produces a differential response at its outputs having a common mode potential which is one-half the magnitude of the sensor excitation voltage. Various circuit techniques are known which will result in a simulated Wheatstone bridge response having such characteristics. One such technique is disclosed in U.S. Pat. No. 4,745,047, and could be incorporated within the interface circuit 10. However, for most patient monitors, the differential characteristics of a true Wheatstone bridge response is not necessary for proper operation.

The interface circuit 10 can thus be used to interface electrical transducer sensors with many different types of monitors 18, regardless of the format of the monitor's excitation power and in spite of the fact that the monitor has been designed to be used only with a standard strain gauge transducer. Further, the transducer sensor can utilize a standard electrical Wheatstone bridge-type circuit, and yet the interface circuit 10 will provide complete electrical isolation between the transducer 12 and the monitor 18. Because there are no electrically conductive connections between the transducer and the monitor, there is no possibility of any harmful currents flowing between the patient and the monitor. In addition to providing this electrical isolation, the circuit 10 derives all of its electrical power from the excitation signal supplied by the monitor, thereby eliminating the need for an independent source of circuit power.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Patent is:

1. An interface circuit for use in a system which measures a physiological condition within a patient, the interface circuit comprising:

a physiological sensor device;

bipolar supply means for electrically receiving an excitation power signal generated by an excitation source, and for deriving therefrom at least one unregulated power supply voltage, the at least one unregulated supply voltage having a magnitude that is proportional to the magnitude of said excitation power signal;

voltage conversion means, responsive to said at least one unregulated power supply voltage, for providing at least one fixed output supply voltage and a sensor excitation signal for use as an excitation signal for said physiological sensor device; and bypass means for selectively operating the interface circuit in either an A.C. operating mode when the excitation power signal is A.C., or in a D.C. bypass mode when the excitation power signal is D.C.

2. An interface circuit as defined in claim 1, wherein the excitation power signal is a voltage having a magnitude and a frequency selected from any one of a plurality of magnitude and frequency values.

3. An interface circuit as defined in claim 1, wherein the physiological sensor device is a semiconductor transducer having a Wheatstone bridge-type circuit formed thereon.

4. An interface circuit as defined in claim 1, wherein the excitation source is a patient vital signs monitor.

5. An interface circuit as defined in claim 1, further comprising A.C. power filter means for simulating an impedance of a resistive network and thereby preventing the excitation power signal from being distorted.

6. An interface circuit as defined in claim 1, wherein the at least one unregulated supply voltage includes a positive and a negative supply voltage having substantially equal but opposite polarities, and wherein the positive and negative supply voltages have substantially only D.C. components.

7. An interface circuit as defined in claim 1, wherein the voltage conversion means comprises means for electrically isolating the sensor excitation signal from the excitation power signal.

8. An interface circuit as defined in claim 1, further comprising:

means for receiving a sensor output signal generated by said sensor device in response to said sensor excitation signal, and for providing a response signal that is representative of a value that is proportional to the magnitude of the physiological condition detected by the sensor device; and scaling means, responsive to said response signal, for providing a parameter signal having a magnitude that is proportional to the magnitude of the excitation power signal and that is also proportional to the magnitude of the physiological condition.

9. An interface circuit as defined in claim 8, wherein the receiving means includes means for electrically isolating the sensor output signal from the response signal.

10. An interface circuit as defined in claim 8, further comprising attenuation means for attenuating the parameter signal to a predetermined nominal scale factor, thereby providing a simulated sensor signal.

11. An interface circuit for use in a system which measures a physiological condition within a patient, the interface circuit comprising:

a physiological sensor device;

power supply means for receiving an excitation power signal generated by an excitation source, and for deriving therefrom at least one supply voltage and a sensor excitation signal for use as an excitation signal for said physiological sensor device;

means for receiving a sensor output signal generated by said sensor device in response to said sensor excitation signal, and for providing a response signal that is representative of a value that is proportional to a magnitude of the physiological condition detected by the sensor device;

scaling means, responsive to said response signal, for providing a parameter signal having a magnitude that is proportional to the magnitude of the excitation power signal and that is also proportional to the magnitude of the physiological condition; and bypass means for selectively operating the interface circuit in either an A.C. operating mode when the excitation power signal is A.C., or in a D.C. bypass mode when the excitation power signal is D.C.

12. An interface circuit as defined in claim 11, wherein the physiological sensor device is a semiconductor transducer having a Wheatstone bridge-type circuit formed thereon.

13. An interface circuit as defined in claim 11, wherein the excitation source is a patient vital signs monitor.

14. An interface circuit as defined in claim 11, wherein the at least one supply voltage includes a positive and a negative unregulated power supply voltage, and a fixed output supply voltage, the positive and the negative unregulated supply voltages being substantially equal but opposite in polarity and having magnitudes which are proportional to the magnitude of the excitation power signal.

15. An interface circuit as defined in claim 11, wherein the excitation power signal is a voltage having a magnitude and a frequency selected from any one of a plurality of magnitude and frequency values.

16. An interface circuit as defined in claim 11, further comprising A.C. power filter means for simulating an impedance of a resistive network and thereby preventing the excitation power signal from being distorted.

17. An interface circuit as defined in claim 11, wherein the power supply means comprises means for electrically isolating the sensor excitation signal from the excitation power signal.

18. An interface circuit as defined in claim 11, wherein the receiving means includes means for electrically isolating the sensor output signal from the response signal.

19. An interface circuit as defined in claim 11, further comprising attenuation means for attenuating the parameter signal to a predetermined nominal scale factor, thereby providing a simulated sensor signal.

20. An interface circuit for use in a system which measures a physiological condition within a patient, the interface circuit comprising:

a physiological sensor device;

bipolar supply means for electrically receiving an excitation power signal generated by an excitation source, and for deriving therefrom at least one unregulated power supply voltage, the at least one unregulated supply voltage having a magnitude that is proportional to the magnitude of said excitation power signal;

voltage conversion means, responsive to said at least one unregulated power supply voltage, for providing at least one fixed output supply voltage and a sensor excitation signal for use as an excitation signal for said physiological sensor device;

means for receiving a sensor output signal generated by said sensor device in response to said sensor excitation signal, and for providing a response signal that is representative of a value that is proportional to a magnitude of the physiological condition detected by the sensor device;

scaling means, responsive to said response signal, for providing a parameter signal having a magnitude that is proportional to the magnitude of the excitation power signal and that is also proportional to the magnitude of the physiological condition; and bypass means for selectively operating the interface circuit in either an A.C. operating mode when the excitation power signal is A.C., or in a D.C. bypass mode when the excitation power signal is D.C.

21. An interface circuit as defined in claim 20, wherein the physiological sensor device is a semiconductor transducer having a Wheatstone bridge-type circuit formed thereon.

22. An interface circuit as defined in claim 21, wherein the excitation source is a patient vital signs monitor.

23. An interface circuit as defined in claim 22, wherein the excitation power signal is a voltage having a magnitude and a frequency selected from any one of a plurality of magnitude and frequency values.

24. An interface circuit as defined in claim 23, wherein the at least one unregulated supply voltage includes a positive and a negative unregulated power supply voltage having substantially equal but opposite polarities, and wherein the positive and negative supply voltages have substantially only D.C. components.

25. An interface circuit as defined in claim 24, further comprising A.C. power filter means for simulating an impedance of a resistive network and thereby preventing the excitation power signal from being distorted.

26. An interface circuit as defined in claim 25 wherein the voltage conversion means comprises means for electrically isolating the sensor excitation signal from the excitation power signal.

27. An interface circuit as defined in claim 26, wherein the receiving means includes means for electrically isolating the sensor output signal from the response signal.

28. An interface circuit as defined in claim 27, further comprising attenuation means for attenuating the parameter signal to a predetermined nominal scale factor, thereby providing a simulated sensor signal.

29. An interface circuit for use in a system which measures a physiological condition within a patient, the interface circuit comprising:

bipolar supply means for electrically receiving an excitation power signal generated by an excitation source, and for deriving therefrom at least one unregulated power supply voltage, the at least one supply voltage having a magnitude that is proportional to the magnitude of said excitation power signal; and voltage conversion means, responsive to said at least one unregulated power supply voltage, for providing at least one fixed output supply voltage and a sensor excitation signal for use as an excitation signal for a physiological sensor device, the voltage conversion means including:

means for electrically isolating the sensor excitation signal from the excitation power signal.

30. An interface circuit for use in a system which measures a physiological condition within a patient, the interface circuit comprising:

a physiological sensor device;

power supply means for receiving an excitation power signal generated by an excitation source, and for deriving therefrom at least one supply voltage and a sensor excitation signal for use as an excitation signal for said physiological sensor device, the power supply means including means for electrically isolating the sensor excitation signal from the excitation power signal;

means for receiving a sensor output signal generated by said sensor device in response to said sensor excitation signal, and for providing a response signal that is representative of a value that is proportional to a magnitude of the physiological condition detected by the sensor device, the receiving means including means for electrically isolating the sensor output signal from the response signal; and scaling means, responsive to said response signal, for providing a parameter signal having a magnitude that is proportional to the magnitude of the excitation power signal and that is also proportional to the magnitude of the physiological condition.

31. An interface circuit as defined in claim 30, wherein the physiological sensor device is a semiconductor transducer having a Wheatstone bridge-type circuit formed thereon.

32. An interface circuit as defined in claim 30, wherein the excitation source is a patient vital signs monitor.

33. An interface circuit as defined in claim 30, wherein the excitation power signal is a voltage having a magnitude and a frequency selected from any one of a plurality of magnitude and frequency values.

34. An interface circuit as defined in claim 30, wherein the at least one supply voltage includes a positive and a negative unregulated power supply voltage, and a fixed output supply voltage, the positive and the negative unregulated supply voltages being substantially equal but opposite in polarity and having magnitudes which are proportional to the magnitude of the excitation power signal, and wherein the positive and negative supply voltages have substantially only D.C. components.

35. An interface circuit as defined in claim 30, further comprising A.C. power filter means for simulating an impedance of a resistive network and thereby preventing the excitation power signal from being distorted.

36. An interface circuit as defined in claim 30, further comprising bypass means for selectively operating the interface circuit in either an A.C. operating mode when the excitation power signal is A.C., or in a D.C. bypass mode when the excitation power signal is D.C.

37. An interface circuit for use in a system which measures a physiological condition within a patient, the interface circuit comprising:

a physiological sensor device;

bipolar supply means for electrically receiving an excitation power signal generated by an excitation source, and for deriving therefrom a positive and a negative unregulated power supply voltage, the supply voltages having magnitudes that are substantially equal but opposite in polarity and which are both proportional to the magnitude of said excitation power signal;

voltage conversion means, responsive to either of said positive or negative unregulated power supply voltages, for providing at least one fixed output supply voltage and a sensor excitation signal for use as an excitation signal for said physiological sensor device, the voltage conversion means including means for electrically isolating the sensor excitation signal from the excitation power signal;

means for receiving a sensor output signal generated by said sensor device in response to said sensor excitation signal, and for providing a response signal that is representative of a value that is proportional to the magnitude of the physiological condition detected by the sensor device, the receiving means including means for electrically isolating the sensor output signal from the response signal; and scaling means, responsive to said response signal, for providing a parameter signal having a magnitude that is proportional to the magnitude of the excitation power signal and that is also proportional to the magnitude of the physiological condition.

38. An interface circuit as defined in claim 37, wherein the physiological sensor device is a semiconductor transducer having a Wheatstone bridge-type circuit formed thereon.

39. An interface circuit as defined in claim 38, wherein the excitation source is a patient vital signs monitor.

40. An interface circuit as defined in claim 39, wherein the excitation power signal is a voltage having a magnitude and a frequency selected from any one of a plurality of magnitude and frequency values.

41. An interface circuit as defined in claim 40, further comprising A.C. power filter means for simulating an impedance of a resistive network and thereby preventing the excitation power signal from being distorted.

42. An interface circuit as defined in claim 41, further comprising bypass means for selectively operating the interface circuit in either a A.C. operating mode when the excitation power signal is A.C., or in a D.C. bypass mode when the excitation power signal is D.C.

* * * * *